United States Patent [19]

Shultz

[11] Patent Number: 4,466,430

[45] Date of Patent: Aug. 21, 1984

[54] SURGICAL DRAPE WITH INSTRUMENT SUPPORT

[75] Inventor: Jay S. Shultz, Roswell, Ga.

[73] Assignee: Kimberly-Clark Corporation, Neenah, Wis.

[21] Appl. No.: 391,369

[22] Filed: Jun. 23, 1982

[51] Int. Cl.³ ............................................. A61F 13/00
[52] U.S. Cl. ............................................... 128/132 D
[58] Field of Search ..................... 128/132 D, 132 R; 2/255, 261

[56] References Cited

U.S. PATENT DOCUMENTS

| Re. 26,759 | 1/1970 | Melges . | |
|---|---|---|---|
| Re. 27,710 | 7/1973 | Melges . | |
| 3,410,266 | 6/1966 | Krzewinski et al. | 128/132 D |
| 3,482,567 | 4/1967 | Franklin | 128/132 D |
| 3,494,356 | 2/1970 | Melges . | |
| 3,561,439 | 2/1971 | Bayer . | |
| 3,654,047 | 4/1972 | Berkowitz . | |
| 3,668,050 | 6/1972 | Donnelly . | |
| 3,727,658 | 4/1973 | Eldridge, Jr. . | |
| 3,738,359 | 6/1973 | Linquist et al. . | |
| 3,856,006 | 2/1974 | Krzewinski . | |
| 3,882,859 | 5/1975 | Ericson . | |
| 3,934,587 | 1/1976 | Gordon | 128/132 D |

Primary Examiner—Richard J. Apley
Assistant Examiner—Greg Beaucage
Attorney, Agent, or Firm—William D. Herrick; R. Jonathan Peters; Howard Olevsky

[57] ABSTRACT

A surgical drape sheet has an instrument support table incorporated in the structure of the sheet. The table is provided by a flat sheet of plastic or cardboard located between the base sheet and fenestration area reinforcement fabric and stabilized against lateral movement.

4 Claims, 2 Drawing Figures

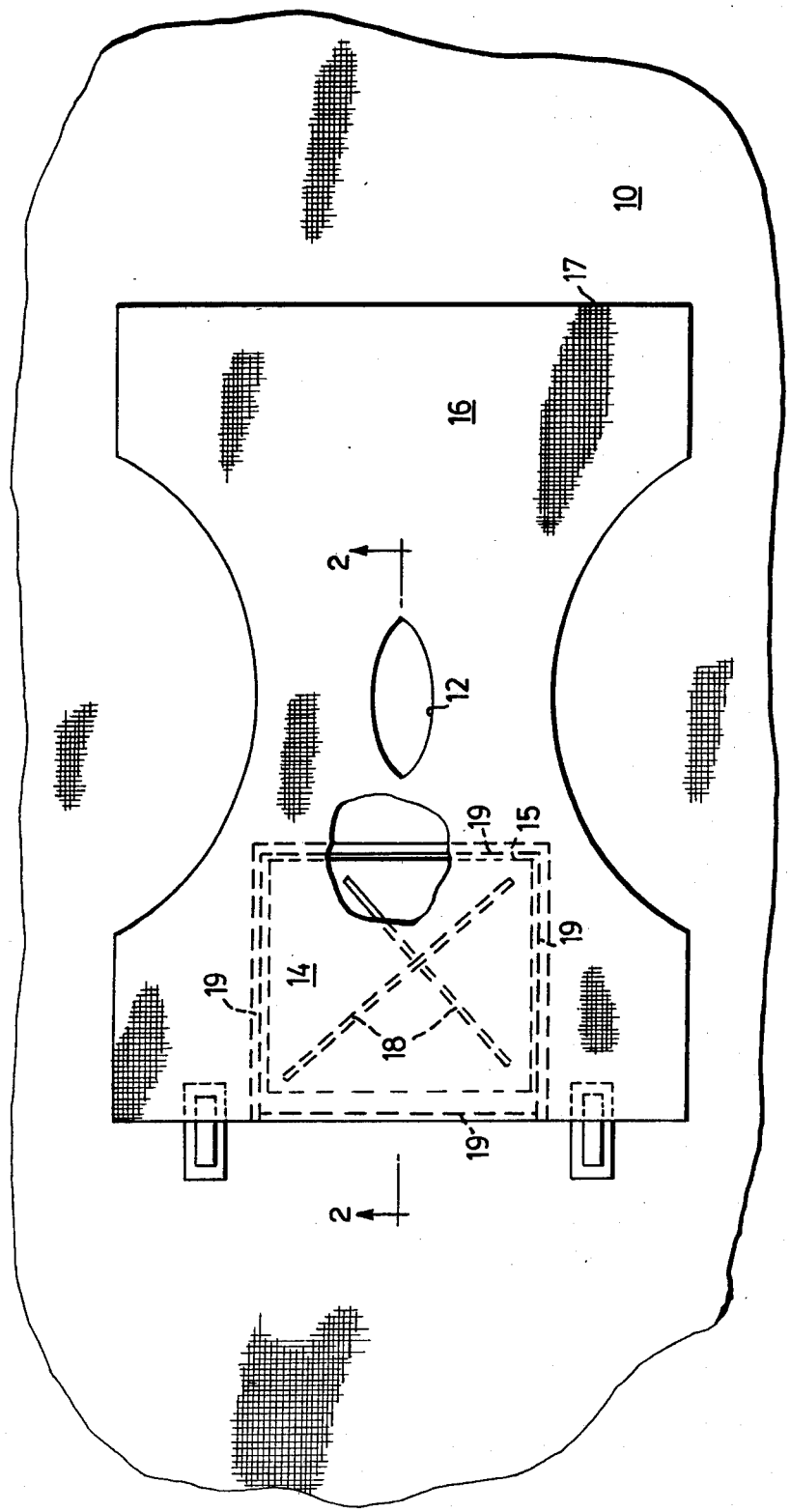
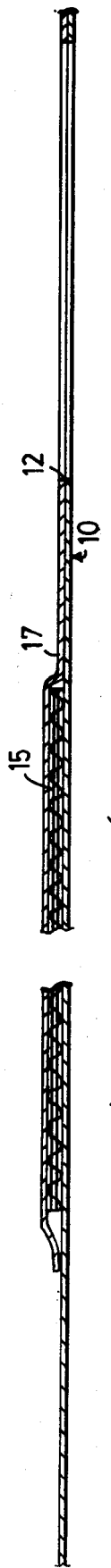
FIG. 1
FIG. 2

SURGICAL DRAPE WITH INSTRUMENT SUPPORT

TECHNICAL FIELD

This invention relates generally to surgical drape sheets and, more particularly, to disposable surgical drape sheets having provision for support of instruments.

BACKGROUND ART

Disposable surgical drape sheets have been in widespread commercial use which are made of a material having a high frictional coefficient in the area surrounding the fenestration to provide a non-slip surface and prevent the dislodgement of surgical instruments and the like which are placed on the sheet in that area during an operational procedure. A non-slip surface may be provided, for example, by a fluid absorbent flexible plastic foam layer on the surface of the drape sheet adjacent the fenestration, as disclosed in commonly assigned U.S. Pat. No. 3,668,050. Other proposals have come forth for fastening instrument support pads on the surface of the drape sheet. In all such cases, the non-slip surface or instrument support pads have been relatively flexible in construction to conform to the shape of the patient's body where it rests thereon. This has the result that in some operational procedures, due to the placement of the drape sheet, the non-slip surface or instrument support pads will be steeply inclined and instruments or the like placed thereon will slide off, despite the high frictional coefficient of the surface.

DISCLOSURE OF INVENTION

The primary aim of this invention is to provide disposable surgical drapes with instrument support sections that are rigid so as to be self-supporting and capable of being placed and maintained in a substantially level position to provide a resting place for instruments or the like spaced from the fenestration.

Another object is to provide a disposable surgical drape sheet having an essentially rigid instrument support table incorporated within the structure of the drape sheet.

BRIEF DESCRIPTION OF THE DRAWING:

Other objects will become apparent from the following description taken in connection with the accompanying drawings in which:

FIG. 1 is a fragmentary plan view of a disposable surgical drape having an instrument support table incorporated therein according to the invention; and FIG. 2 is a fragmentary sectional view taken substantially in the plane of lines 2—2 in FIG. 1.

BEST MODE FOR CARRYING OUT THE INVENTION:

Turning now to the drawings, the illustrative surgical drape sheet shown in FIG. 1 includes a base sheet 10 of surgical drage fabric provided with a fenestration 12. Suitable fabrics are fibrous materials such as laminates of cellulosic wadding with scrim reinforcement or three ply laminates of spun-bonded continuous filament webs as the outer plies and a mat of discontinuous meltblown polymeric microfibers, preferably prolypropylene, sandwiched between the outer plies, the three ply structure being intermittently bonded by heat and pressure as described in commonly assigned Brock et al, U.S. Pat. No. 4,041,203. For this invention, such three ply laminates are preferred for the base sheet 10, having a basis weight of about 1.0 to 2.5 oz/yd$^2$ containing at least about 0.5 oz/yd$^2$ of the microfiber mat, such laminates being liquid repellent, permeable and treated to reduce surface resistivity to a satisfactory level for hospital use.

The base sheet 10 of the drape is reinforced surrounding the fenestration 12 providing a primary operative area 16. The reinforcement is preferably provided by a liquid impervious fabric 17 attached to the base sheet 10 of the drape and covering the primary operative area 16. Attachment may be achieved in various ways. However, an adhesive bond with adhesive around the outside perimeter of the operative area 16 and also around the perimeter of the fenestration 12 is presently preferred. The fabric used for the reinforcement of the primary operative area 16 is preferably a barrier fabric in the form of a laminate of a continuous filament web, a mat of meltblown polymeric microfibers and a polymeric film heat and pressure bonded to provide a unitary structure as disclosed in co-pending application of Jay Shultz and Joseph D. Wahliquist, Ser. No. 15076, filed May 30, 1983, entitled "Impervious Absorbent Barrier Fabric Embodying Films And Fibrous Webs", now U.S. Pat. No. 4,379,192. The reinforcement fabric 17 in the area 16 is desirably liquid impervious, absorbent, strong, lint free, abrasion resistant, as well as flexible, to prevent strike-through of liquid and contamination of the operative site by the passage of liquids and bacteria while absorbing liquids to prevent contamination of the site and run-off. Preferably the reinforcement fabric 17, when formed as a laminate, as previously described, has about the same basis weight as the base sheet 10. Other fabrics may be used for reinforcement such as a film-foam laminate, having a fluid impervious polyethylene film and a layer of polyurethane foam as disclosed in commonly assigned U.S. Pat. No. 3,668,050.

According to this invention, incorporated in the drape sheet spaced from the fenestration 12 is an instrument support section 14 provided by a rigid member 15 between the base sheet 10 and the reinforcement barrier fabric 17, the section 14 providing a flat table on which instruments may be placed during an operational procedure. The instrument support section 14 is preferably located along the center line of the drape sheet so that it will rest on the patient when the patient is covered by the drape sheet and lying in a supine position. Because of the rigidity of the member 15 however, the instrument support section 14 is not required to rest on the patient but may be placed in position adjacent the patient's body and braced in a substantially horizontal plane by towels or the like to provide a substantially horizontal support table; similarly, the support section 14 may be placed over a portion of the patient's body which is very irregular, where extensive bracing may be required to level the table 14.

In carrying out the invention, moreover, the flat rigid member 15 is fixed against lateral movement between the base sheet 10 and the reinforcement fabric 17 so that, once being placed in position and braced, the instrument support section 14 will be stabilized with the drape sheet itself against movement. For this purpose, the support member 15, which may be made of a stiff sheet of plastic or cardboard, a sheet of cardboard about 6"×6" in size being preferred as shown in FIG. 2, is adhered to the base sheet 10, the reinforcement fabric 17, or both, by adhesive 18 or a like agent. Plastic or wire formed into a flat, stiff member 15 may be employed instead of sheet material, but whatever the form of the material, it should be stabilized against movement relative to the underlying base sheet 10 and the overlying reinforcement fabric 17. The size of the support member 15 may be varied depending on the type of drape, the 6"×6" size being most suitable for a laparotomy drape, for example.

As an alternative construction for stabilizing the support member 15, a pocket may be provided between the base sheet 10 and the fabric 17 for receiving the member 15 by glue lines 19 around the border of the member 15 attaching the base sheet 10 to the fabric 17.

When the fabrics forming the base sheet 10 and reinforcement fabric 17 in the area 16 are the preferred materials, such fabrics have sufficient strength to withstand without rupture the strain at localized areas, such as at the edges and corners of the rigid support member 15 where it tends to poke through these fabrics. The three ply laminate base sheet fabric 10 has particularly high energy absorption characteristics, making it especially suitable in such applications. With the impervious reinforcement fabric 17 overlying the support member 15, penetration is prevented of body fluids, water, sterilizing or disinfecting solution that may be on the instruments placed on the section 14. Furthermore, the preferred reinforcement fabrics provide an exposed, cushioned surface for receiving instruments that has a high coefficient of friction, at least 20 degrees, measured by the procedure described in said copending application, to restrain the instruments from sliding off even when the support section 14 is not perfectly level. While other fabrics may be used for the reinforced area 16, the advantage of the preferred fabric is that it has a structure satisfying the functional requirements of a covering for the support section 14, namely, that it be strong, be liquid impervious, have a high coefficient of friction and provide an abrasion resistant, lint free surface to avoid production of lint that may contaminate the operative site.

I claim:

1. A surgical drape sheet comprising:
   a flexible fibrous base sheet having a primary operative area including a fenestration area;
   a flexible liquid impervious fabric covering said primary operative area and attaching to said base sheet;
   a flat, rigid inflexible member between said base sheet and said liquid repellent fabric and providing an instrument support section built into said drape sheet spaced from said fenestration; and
   means for fixing said member against lateral movement between said base sheet and fabric.

2. A surgical drape sheet according to claim 1 wherein said member is adhered to either said base sheet or fabric to fix said member against lateral movement.

3. A surgical drage sheet according to claim 1 wherein said member is adhered to both said fabric and base sheet to fix said member against lateral movement.

4. A surgical drape sheet according to claim 1 wherein a section of said base sheet and fabric are unattached and define a pocket in said unattached section; and said member is located in said pocket to fix said member against lateral movement.

* * * * *

UNITED STATES PATENT AND TRADEMARK OFFICE
CERTIFICATE OF CORRECTION

PATENT NO. : 4,466,430

DATED : August 21, 1984

INVENTOR(S) : Jay S. Shultz

It is certified that error appears in the above-identified patent and that said Letters Patent is hereby corrected as shown below:

Column 1, line 14, "attaching" should be -- attached --.

Signed and Sealed this

Thirtieth Day of April 1985

[SEAL]

Attest:

DONALD J. QUIGG

Attesting Officer      Acting Commissioner of Patents and Trademarks